United States Patent
Tofighi et al.

(10) Patent No.: US 6,840,961 B2
(45) Date of Patent: Jan. 11, 2005

(54) MACHINABLE PREFORMED CALCIUM PHOSPHATE BONE SUBSTITUTE MATERIAL IMPLANTS

(75) Inventors: Aliassghar N. Tofighi, Waltham, MA (US); Michele Krause, Wayne, NJ (US); Dosuk D. Lee, Brookline, MA (US)

(73) Assignee: Etex Corporation, Cambridge, MA (US)

( * ) Notice: Subject to any disclaimer, the term of this patent is extended or adjusted under 35 U.S.C. 154(b) by 0 days.

(21) Appl. No.: 10/027,656

(22) Filed: Dec. 21, 2001

(65) Prior Publication Data

US 2003/0135283 A1 Jul. 17, 2003

(51) Int. Cl.⁷ .............................. A61F 2/28; A61F 13/00; A61F 2/00; A01N 59/26; A61K 33/42
(52) U.S. Cl. ..................... 623/23.61; 424/422; 424/423; 424/601; 424/602
(58) Field of Search .......................... 623/11.11, 16.11, 623/17.11, 17.12, 17.13, 17.14, 17.15, 17.16, 23.51, 23.57, 23.61

(56) References Cited

U.S. PATENT DOCUMENTS

| | | | |
|---|---|---|---|
| 5,336,264 A | * | 8/1994 | Constanz et al. ............. 623/16 |
| 5,383,615 A | | 1/1995 | Calka et al. ................. 241/172 |
| 5,508,342 A | | 4/1996 | Antonucci et al. ........... 524/788 |
| 5,650,176 A | | 7/1997 | Lee et al. ..................... 424/602 |
| 5,676,976 A | | 10/1997 | Lee et al. ..................... 424/602 |
| 5,679,294 A | | 10/1997 | Umezu et al. ................. 264/44 |
| 5,683,461 A | | 11/1997 | Lee et al. ..................... 623/16 |
| 5,837,030 A | | 11/1998 | Schultz et al. ................. 75/352 |
| 5,872,074 A | | 2/1999 | Schultz et al. .............. 502/328 |
| 5,900,254 A | | 5/1999 | Constantz .................... 424/602 |
| 5,916,381 A | | 6/1999 | Sapru et al. ................. 148/403 |
| 6,005,162 A | | 12/1999 | Constantz ..................... 623/16 |
| 6,013,591 A | * | 1/2000 | Ying et al. ..................... 501/1 |
| 6,017,504 A | | 1/2000 | Kaliaguine et al. .......... 423/263 |
| 6,027,742 A | | 2/2000 | Lee et al. .................... 424/602 |
| 6,117,456 A | | 9/2000 | Lee et al. .................... 424/602 |
| 6,132,463 A | | 10/2000 | Lee et al. ..................... 623/16 |
| 6,139,578 A | | 10/2000 | Lee et al. ................. 623/16.11 |
| 6,187,329 B1 | * | 2/2001 | Agrawal et al. ............. 424/426 |
| 6,201,039 B1 | * | 3/2001 | Brown et al. ................ 523/115 |
| 6,214,368 B1 | | 4/2001 | Lee et al. .................... 424/423 |
| 6,277,151 B1 | | 8/2001 | Lee et al. ................. 623/23.61 |
| 6,287,341 B1 | | 9/2001 | Lee et al. ................. 623/16.11 |
| 6,331,312 B1 | | 12/2001 | Lee et al. .................... 424/426 |
| 6,334,891 B1 | | 1/2002 | Constantz et al. ............. 106/35 |

FOREIGN PATENT DOCUMENTS

WO    WO 98/16268    4/1998

* cited by examiner

Primary Examiner—Kevin Shaver
Assistant Examiner—Anuradha Ramana
(74) Attorney, Agent, or Firm—Paul T. Clark; Clark & Elbing LLP

(57) ABSTRACT

The present invention provides machinable calcium phosphate bone substitute material implants having mechanical properties comparable to those of natural bone. The implants include intimately mixed solid precursor materials that react under physiological conditions to form poorly-crystalline hydroxyapatite and eventually are remodeled into bone in vivo. The implants can include a biocompatible polymer to increase density and strength and control resorbability.

40 Claims, 3 Drawing Sheets

MACHINABLE PREFORMED CALCIUM PHOSPHATE BONE SUBSTITUTE MATERIAL IMPLANTS

BACKGROUND OF THE INVENTION

1. Field of the Invention

The field of the present invention is bone repair and replacement. More specifically, the invention relates to machinable synthetic bone substitute material implants having mechanical properties comparable to those of natural bone.

2. Summary of the Related Art

Treatments for bone voids, defects, and injuries must provide structural integrity and induce the formation of new bone. In particular, spinal fusion is designed to stabilize the spinal column by creating a bridge between adjacent vertebrae in the form of a bone fusion mass. Early spinal fusion methods involved stabilizing the spinal column with a metal plate or rod spanning the affected vertebrae and allowing bone fusion to occur around the implanted hardware. Various other forms of metal implants have also been used in spinal fusion procedures. However, the strength of metal implants causes stress shielding of the surrounding bone, which slows the natural bone growth that leads to fusion. Further, metal implants are permanent foreign bodies that cannot be remodeled into natural bone in vivo. In addition, many surgical procedures for implanting metal devices are long and complex.

Natural bone grafts have been used to promote osteogenesis and to avoid the disadvantages of metal implants. Naturally-occurring bone mineral is made of nanometer-sized, poorly-crystalline calcium phosphate of hydroxyapatite structure with a Ca/P ratio between 1.5 and 1.7. These properties impart solubility to bone tissue that allows it to be repaired continually by osteoclasts and osteoblasts. Natural bone grafts are incorporated into a patient's bone through this continual remodeling process in vivo. However, natural bone grafts are associated with problems such as limited availability and painful, risky harvesting procedures for a patient's own autogenous bone, and risks of viral transmission and immune reaction for allograft bone from a cadaver.

Synthetic bone graft materials have been used to avoid the problems associated with natural bone grafts. Desirable properties for synthetic bone graft materials include the following: chemical biocompatibility with natural bone; structural integrity, so that the graft remains in place and intact until bone heals around it; resorbability, so that the foreign material is replaced by bone and is accessible by osteoclasts, osteoblasts, and other bone-forming cells; and compatibility with low-temperature processing, which is required for incorporating heat-sensitive bone growth proteins to stimulate osteoblasts. Bioceramics have been used as bone graft substitute materials, providing a matrix that encourages new bone growth. Most commonly used have been the calcium phosphate ceramics hydroxyapatite and tricalcium phosphate. Hydroxyapatite is chemically similar to and biocompatible with natural bone. Highly crystalline hydroxyapatite has been produced that is dense, and therefore strong. However, such crystalline hydroxyapatite is essentially insoluble in vivo, and thus is not replaced by natural bone. Hydroxyapatite solids of lower crystallinity have been reported that are resorbable, but are not strong enough for spinal fusion applications or other applications requiring high-strength materials. Similarly, tricalcium phosphate materials generally are degraded rapidly in vivo, but lack sufficient strength for weight-bearing applications. Combinations of hydroxyapatite and tricalcium phosphate have been reported, which attempt to mitigate the shortcomings of the individual calcium phosphate components.

A ceramic implant of high strength and having the biological properties of natural bone, without the disadvantages of prior art materials, has proven elusive. Thus, a need remains in the art for bone substitute material implants that are biocompatible and resorbable, yet strong enough for use in applications requiring high strength, for example, in spinal fusion applications to support the spinal column until adjacent vertebrae have fused.

SUMMARY OF THE INVENTION

The present invention provides machinable bone substitute material implants that have mechanical properties comparable to those of natural bone and are capable of remodeling into bone in vivo. The implants, which provide sufficient strength for use in spinal fusion, include intimately mixed precursor materials that react under physiological conditions to form poorly-crystalline hydroxyapatite and that eventually reform into bone, e.g., remodel.

Accordingly, in one aspect, the invention provides a bone implant comprising a calcium phosphate precursor capable of forming poorly-crystalline hydroxyapatite in vivo. The precursor has a calcium to phosphorous atomic ratio between about 1.2 and about 1.68, and the implant has a compressive strength of at least about 60 MPa.

In some embodiments, the implant is a machined article. In some embodiments, the precursor comprises a first calcium phosphate in intimate mixture with a second calcium phosphate having a different calcium to phosphorous atomic ratio than the first calcium phosphate. In some embodiments, the precursor comprises a first calcium phosphate in intimate mixture with a second calcium phosphate having a different degree of crystallinity than the first calcium phosphate. In some such embodiments, the first calcium phosphate is an amorphous calcium phosphate and the second calcium phosphate has greater crystallinity than the first calcium phosphate. In particular embodiments, the first calcium phosphate has a calcium to phosphorous atomic ratio less than about 1.5. In some embodiments, the second calcium phosphate is selected from the group consisting of dicalcium phosphate dihydrate, calcium metaphosphate, heptacalcium phosphate, tricalcium phosphate, calcium pyrophosphate dihydrate, calcium pyrophosphate, and octacalcium phosphate. In particular embodiments, the second calcium phosphate is dicalcium phosphate dihydrate. In some embodiments, the bone implant further comprises a biocompatible polymer powder. In other embodiments, the bone implant further comprises a biocompatible polymer fiber. In some embodiments, the bone implant has a compressive strength of at least about 120 MPa.

In another aspect, the invention provides a bone implant comprising a calcium phosphate precursor capable of forming poorly-crystalline hydroxyapatite in vivo. The precursor has a calcium to phosphorous atomic ratio between about 1.2 and about 1.68, and the implant has a porosity between about 5% and about 30%.

In still another aspect, the invention provides a bone implant comprising a calcium phosphate precursor capable of forming poorly-crystalline hydroxyapatite in vivo. The precursor has a calcium to phosphorous atomic ratio between about 1.2 and about 1.68 and a particle size less than about 125 μm.

In yet another aspect, the invention provides a bone implant comprising, in intimate mixture, a first calcium phosphate that is an amorphous calcium phosphate and a second calcium phosphate having greater crystallinity than the first calcium phosphate. The overall calcium to phosphorous atomic ratio is between about 1.2 and about 1.68, and the implant has and a compressive strength of at least about 60 MPa.

In some embodiments, the first calcium phosphate has a calcium to phosphorous atomic ratio less than about 1.5. In some embodiments, the second calcium phosphate is selected from the group consisting of dicalcium phosphate dihydrate, calcium metaphosphate, heptacalcium phosphate, tricalcium phosphate, calcium pyrophosphate dihydrate, calcium pyrophosphate, and octacalcium phosphate. In particular embodiments, the second calcium phosphate is dicalcium phosphate dihydrate. In some embodiments, the bone implant further comprises a biocompatible polymer powder. In other embodiments, the bone implant further comprises a biocompatible polymer fiber. In some embodiments, the bone implant has a compressive strength of at least about 120 MPa.

In another aspect, the invention provides a method of bone implantation. The method comprises providing a bone implant comprising a calcium phosphate precursor capable of forming poorly-crystalline hydroxyapatite in vivo. The precursor has a calcium to phosphorous atomic ratio between about 1.2 and about 1.68, and the implant has a compressive strength of at least about 60 MPa. The method further comprises securing the bone implant at a site requiring implantation. The precursor undergoes conversion to poorly-crystalline hydroxyapatite at the implantation site. In some embodiments, conversion of the precursor to poorly-crystalline hydroxyapatite is completed in a time between about 2 weeks and about 6 weeks after securing the bone implant at the implantation site. In some embodiments, conversion of the precursor to poorly-crystalline hydroxyapatite occurs at about body temperature but does not proceed significantly at room temperature.

In still another aspect, the invention provides a method of bone implantation comprising providing a bone implant. The bone implant comprises, in intimate mixture, a first calcium phosphate that is an amorphous calcium phosphate and a second calcium phosphate having greater crystallinity than the first calcium phosphate. The overall calcium to phosphorous atomic ratio is between about 1.2 and about 1.68, and the implant has a compressive strength of at least about 60 MPa. The method further comprises securing the bone implant at a site requiring implantation. The first and second calcium phosphates undergo conversion to poorly-crystalline hydroxyapatite at the implantation site. In some embodiments, conversion of the first and second calcium phosphates to poorly-crystalline hydroxyapatite is completed in a time between about 2 weeks and about 6 weeks after securing the bone implant at the implantation site. In some embodiments, conversion of the precursor to poorly-crystalline hydroxyapatite occurs at about body temperature but does not proceed significantly at room temperature.

In another aspect, the invention provides a method of spinal fusion. The method comprises providing a bone implant comprising a calcium phosphate precursor capable of forming poorly-crystalline hydroxyapatite in vivo. The precursor has a calcium to phosphorous atomic ratio between about 1.2 and about 1.68, and the implant has a compressive strength of at least about 60 MPa. The method further comprises securing the bone implant between adjacent spinal vertebrae to promote fusion of the vertebrae.

In yet another aspect, the invention provides a method of spinal fusion comprising providing a bone implant. The bone implant comprises, in intimate mixture, a first calcium phosphate that is an amorphous calcium phosphate and a second calcium phosphate having greater crystallinity than the first calcium phosphate. The overall calcium to phosphorous atomic ratio is between about 1.2 and about 1.68, and the implant has a compressive strength of at least about 60 MPa. The method further comprises securing the bone implant between adjacent spinal vertebrae to promote fusion of the vertebrae.

BRIEF DESCRIPTION OF THE DRAWINGS

The invention is described with reference to the following figures, which are presented for the purpose of illustration only and which are not intended to be limiting of the invention.

DETAILED DESCRIPTION

Figure 1A:
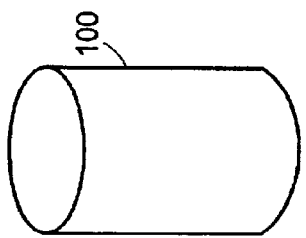
FIG. 1A is a side perspective view of a cylindrical dowel implant of the invention.

The present invention provides bone substitute material implants having high compressive strength and uniform porosity. The implants include intimately mixed solid precursor materials that react under physiological conditions to form poorly-crystalline hydroxyapatite and eventually are remodeled into bone in vivo. The implants can include a biocompatible polymer for increased density and strength. The implants also can include therapeutic agents that are useful at the implantation site, such as antibiotics or bone growth stimulating proteins.

The bone substitute material implants of the invention are made from a calcium phosphate precursor. "Calcium phosphate precursor," as used herein, refers to intimately mixed solid particles of at least two calcium phosphate materials that differ from each other in a property such as, without limitation, Ca/P ratio, crystallinity, or pH, and are capable of reacting with each other under physiological conditions to form poorly-crystalline hydroxyapatite. The precursor can be in the form of a powder or a shaped article pressed therefrom. "Intimately mixed" or "in intimate mixture" means that particles of the two calcium phosphate materials in the precursor are intermixed on a nanometer scale. That is, the calcium phosphate is compositionally homogeneous when analyzed on a micron or greater scale. The mixture can be a physical mixture of the components, they can be mechanically adhered to one another, or the mixture can be a chemical mixture in which the solid state structures of the two calcium phosphate materials are intermixed and pre-reacted at the interfaces between the two components. The intimate integration of the precursor materials allows for their efficient reaction to form poorly-crystalline hydroxyapatite under in vivo conditions, e.g., at body temperature and in physiologically acceptable hydrating media. In some embodiments, the surfaces of the particles of the precursor can be pre-reacted due to the intimate contact between the two components.

The calcium phosphate precursor of the bone substitute material implants of the invention is made up of very small particles. In some embodiments, the particle size is less than about 125 µm. In some embodiments, the particle size is between about 0.1 µm and about 125 µm. In some embodiments, the particle size is between about 0.1 µm and about 50 µm. The small particle size of the precursor corresponds to a high specific surface area, which contributes to efficient reaction of the precursor materials upon exposure to fluids in vivo. For example, the specific surface area of the precursor powder can be between about 50 $m^2/g$ and about 100 $m^2/g$ in the dry powder, and between about 100 $m^2/g$ and about 150 $m^2/g$ after hydration at about body temperature, which causes conversion of the precursor to poorly-crystalline hydroxyapatite. The powder is hydrated by immersion in an aqueous fluid to permit complete wetting of particle surfaces. The small size of the particles of the precursor also contributes to the high density and corresponding high strength of the bone substitute material implants of the invention as densification is performed more readily on smaller particles, which rearrange and pack more easily.

In at least some embodiments, at least one of the materials in the precursor is an amorphous calcium phosphate. Amorphous calcium phosphate is formed by rapid precipitation from a solution containing calcium and phosphate ion sources, which produces very small calcium phosphate nuclei having many defects. Amorphous calcium phosphate initially is formed as a gel-like solid, which can be collected and dried to provide a fine, homogeneous powder. Amorphous calcium phosphate includes solids of varying composition, has a broad, diffuse X-ray diffraction pattern, lacks long-range structure, and is homogeneous when measured on an Angstrom scale.

Amorphous calcium phosphate has a Ca/P ratio in the range of about 1.1 to about 1.9. In some embodiments, the Ca/P ratio is between about 1.40 and about 1.65. In particular embodiments, the Ca/P ratio is between about 1.50 and about 1.58. In some embodiments, the Ca/P ratio is less than about 1.50. In particular embodiments, the Ca/P ratio is between about 1.35 and about 1.49. During the reaction of calcium and phosphate ion sources to form amorphous calcium phosphate, additives can be introduced into solution, and thereby incorporated into the amorphous precipitate structure, to provide desirable properties such as, for example, enhanced amorphicity, increased reactivity to form poorly-crystalline hydroxyapatite, or characteristics that mimic those of natural bone. Non-limiting examples of useful additives include ions such as $CO_3^{2-}$, $Mg^{2+}$, and $P_2O_7^{4-}$. Preparation and characterization of amorphous calcium phosphates is described in detail in U.S. Pat. No. 6,214,368, which is incorporated herein by reference. One method of preparing amorphous calcium phosphate is set forth in Example 1 below.

In at least some embodiments, an amorphous calcium phosphate is combined with at least one other calcium phosphate in the calcium phosphate precursor of the bone substitute material implants of the invention. The second calcium phosphate material differs from the amorphous calcium phosphate, for example in crystallinity, pH, or Ca/P ratio. The second material can be crystalline. Alternatively, the second material can be poorly-crystalline or amorphous, e.g., another amorphous calcium phosphate having a different Ca/P ratio from the first amorphous calcium phosphate. In at least some embodiments, the first calcium phosphate is amorphous and the second calcium phosphate is crystalline. Appropriate second calcium phosphates for use in the calcium phosphate precursor of the invention include acidic, basic, and neutral calcium phosphates having the correct stoichiometry for reaction to obtain apatitic calcium phosphate. Suitable second calcium phosphates include, but are not limited to, dicalcium phosphate dihydrate, calcium metaphosphate, heptacalcium phosphate, tricalcium phosphates, calcium pyrophosphate dihydrate, calcium pyrophosphate, octacalcium phosphate, and additional amorphous calcium phosphates. In at least some embodiments, the first calcium phosphate is neutral, e.g., having a pH between about 6.5 and about 7.0, and the second calcium phosphate is acidic, e.g., having a pH less than about 6.5. Exemplary acidic calcium phosphates include dicalcium phosphate dihydrate, calcium metaphosphate, heptacalcium phosphate, tricalcium phosphates, calcium pyrophosphate dihydrate, calcium pyrophosphate, and octacalcium phosphate. Exemplary neutral calcium phosphates include amorphous calcium phosphate. As described above, the second calcium phosphate material is intimately mixed with the first calcium phosphate material on a nanometer scale approaching the atomic or molecular level in the precursor powder, which has nanometer-sized particles.

The intimately mixed precursor materials of the bone substitute material implants of the invention react efficiently in vivo to form poorly-crystalline hydroxyapatite, the thermodynamically favored form of calcium phosphate. "Poorly-crystalline," as used herein, refers to a material that has very small crystalline domains and therefore is characterized by a broad, poorly-defined X-ray diffraction pattern. "Poorly-crystalline hydroxyapatite" is a poorly crystalline material having small crystalline domains, on the order of those found in naturally-occurring bone, with apatite crystal structure. Poorly-crystalline, rather than highly crystalline, hydroxyapatite is formed from the calcium phosphate precursor of the bone substitute material implants of the invention because the intimately mixed precursor material has no long-range order. The product poorly-crystalline hydroxyapatite of the bone substitute material implants of the invention contains labile environments characteristic of naturally-occurring bone. The poorly-crystalline hydroxyapatite also has a nanometer-scale crystal structure very similar to that of bone. For example, crystalline domains, i.e., the dimension of crystal size, of the poorly-crystalline hydroxyapatite of the implants of the invention can be about 26 nm in length and about 8 nm in width, compared to between about 23 nm and about 32 nm in length and between about 7 nm and about 8 nm in width for natural human bone. The nanometer-scale crystal structure of the poorly-crystalline hydroxyapatite provides a large specific surface area for interaction with the surrounding environment and promotes resorption and remodeling of the bone substitute material.

The poorly-crystalline hydroxyapatite formed from the calcium phosphate precursor of the bone substitute material implants of the invention has a Ca/P ratio similar to that of bone. The Ca/P ratio is between about 1.1 and about 1.9. In some embodiments, the Ca/P ratio is between about 1.2 and about 1.68. In some embodiments, the Ca/P ratio is less than about 1.5. Because the poorly-crystalline hydroxyapatite formation reaction proceeds substantially to completion, all or substantially all of the calcium and phosphate in the precursor materials becomes part of the poorly-crystalline hydroxyapatite product, and the Ca/P ratio of the poorly-crystalline hydroxyapatite can be controlled by the choice of precursor materials.

Figure 1B:
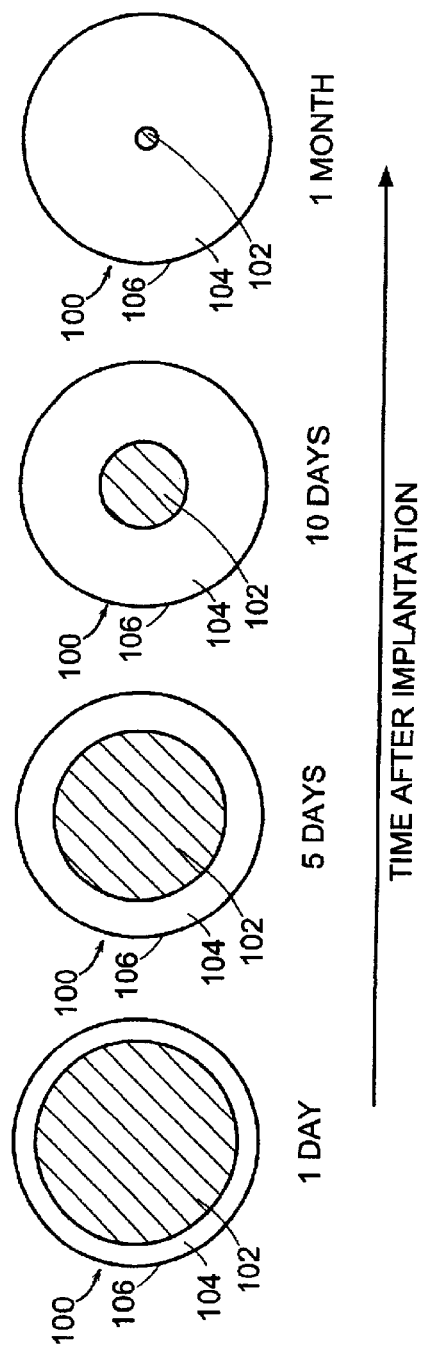
FIG. 1B is a schematic representation of a cross-sectional view of a cylindrical dowel implant of the invention, showing the time scale for reaction of the calcium phosphate precursor materials to form poorly-crystalline hydroxyapatite in vivo.

The calcium phosphate precursor powder of the invention can be shaped and pressed into a very strong, high-density machinable implant for insertion into the body. Upon implantation in vivo, reaction of the precursor to form poorly-crystalline hydroxyapatite begins at the surface of the implant, which is exposed to fluids in the body, and proceeds toward the center of the implant, eventually converting the entire implant to poorly-crystalline hydroxyapatite. The reaction to form poorly-crystalline hydroxyapatite occurs slowly, such that a time period of about one month or more may be required for completion. For example, FIG. 1A shows a bone substitute material dowel in the form of a solid cylinder 100. The dowel is implanted in the body or immersed in an aqueous fluid to hydrate the powder by wetting the powder particle surfaces, and hydration at suitable temperatures, e.g., body temperature, initiates the reaction of the precursor to form poorly-crystalline hydroxyapatite. FIG. 1B is a schematic representation of a cross-sectional view of the cylinder 100, showing that hydration and reaction of the calcium phosphate precursor 102 to form poorly-crystalline hydroxyapatite 104 proceeds slowly inward from the surface 106 of the cylinder 100 over the course of a one-month time period.

Once the calcium phosphate precursor of a bone substitute material implant of the invention has been converted to poorly-crystalline hydroxyapatite, the poorly-crystalline hydroxyapatite is remodeled into bone. As described above, the poorly-crystalline hydroxyapatite has a chemical composition and crystalline structure similar to those of natural bone, and is resorbable in biological systems due to its low crystallinity and/or the presence of stably amorphous apatitic domains. Remodeling involves slow degradation of the poorly-crystalline hydroxyapatite and use by the body of the resulting calcium and phosphate materials to generate new bone. In spinal fusion applications, remodeling accomplishes the fusion of adjacent vertebrae. The high strength of the bone substitute material implants of the invention helps to immobilize the vertebrae until remodeling is complete. Remodeling of the bone substitute material implants of the invention is a long-term process, occurring on a time scale of months to years. For example, a bone substitute material dowel of the invention may be converted fully into bone in about two years. Remodeling proceeds slowly due to the high density of the bone substitute material implants of the invention. The high density and low porosity of the implants slows penetration of the bone substitute material matrix by cells and biological substances, causing remodeling to occur as a long-term inward diffusion process.

Some bone substitute material implants of the invention include a biocompatible polymer in the form of powder or fibers. Polymer powder functions as a binder, while polymer fibers serve as a binder and as reinforcements. "Biocompatible," as used herein, means that the polymer is non-toxic and does not provoke an undesirable physiological, e.g., immune, response. The polymer can also be biodegradable, i.e., it can be degraded in vivo. Examples of suitable biocompatible and/or biodegradable polymers include, without limitation, polylactide, poly(lactide-co-glycolide), polyethyleneimine, polyethylene oxide, polyacrylic acid, polyvinyl alcohol, and polyelectrolytes. Any biocompatible polymer known in the art can be used in implants of the invention. The polymer imparts additional strength to the implants, as demonstrated in Examples 3 and 4 below. Implants including a polymer can be pressed at a temperature above the glass transition temperature of the polymer. Elevated temperatures soften the polymer, allowing it to be compressed more easily and to fill voids between particles of the calcium phosphate materials. This creates an implant having decreased porosity, increased overall density, and improved compressive strength. Implants including a polymer also have increased shear strength, making them especially useful for implantation in dynamic areas of the body, in which the implant and surrounding bone are subjected to a wide range of motion and/or shear stress. Inclusion of a biodegradable polymer also can increase the speed at which an implant is remodeled into bone in vivo. Under physiological conditions, the polymer in the implant degrades more quickly than the surrounding calcium phosphate, creating a macro interconnected pore structure in the implant. This pore structure allows cells in the body to access and act more quickly on the implant, thus accelerating the remodeling process.

Some bone substitute material implants of the invention include one or more bone regenerative proteins (BRPs) to accelerate bone growth and healing. Non-limiting examples of BRPs include transforming growth factor-$\beta$, cell-attachment factors, endothelial growth factors, and bone morphogenetic proteins (Genetics Institute, Cambridge, Mass.; Genentech, Palo Alto, Calif.; Creative Biomolecules, Hopkinton, Mass.). Some bone substitute material implants of the invention include one or more antibiotics to control post-operative inflammation or infection. Exemplary antibiotics include, but are not limited to, penicillin, tetracycline hydrochloride, chlortetracycline hydrochloride, oxytetracycline, chloramphenicol, and gentamicin. Controlled delivery of the BRPs and/or antibiotics is achieved as the bone substitute material implant slowly is degraded and remodeled into bone.

In some embodiments, the bone substitute material implants of the invention are made by high-energy impact milling of the precursor materials, followed by isostatic pressing of the milled powder product. A process for preparing bone substitute material implants is outlined in FIG. 2. First, in step 200, an amorphous calcium phosphate and a second calcium phosphate material are provided in powdered solid form. Optionally, an antibiotic is also included. For example, a powdered solid mixture of about 10 weight percent antibiotic and about 90 weight percent calcium phosphate can be used. Next, in step 202, a high-energy impact ball milling process is performed to achieve densification of the powder, whereby the solids are placed in a jar and ground by randomly moving balls agitated by rotating. Ball milling machines known in the art, such as the Modular Jar Rolling Ball Mill Model 254831M (Paul O. Abbé Inc., Little Falls, N.J.), can be used. The milling breaks down the solid precursor materials into very fine particles that are evenly mixed and dispersed to form a dense, homogeneous product powder. The product powder is characterized by very small particles, which afford high density to the powder, and a lack of long-range crystalline order. In the powder, particles of the two calcium phosphate materials are intermixed on a nanometer scale. This intimate mixture provides for efficient reaction of the precursor materials to form poorly-crystalline hydroxyapatite in vivo.

After milling is complete, in step 204 particle size selection can be performed to obtain a more uniform powder having a desired particle size distribution. In some embodiments, the milled powder is sieved to remove all agglomerates and particles above a certain size, for example above 125 $\mu$m. This particle size exclusion provides a finer powder with a more uniform particle size distribution, which allows for better packing and densification. After particle size selection, in step 205 a polymer powder or fiber optionally is added to the milled powder to increase the strength and resorption rate of the implant produced therefrom. A polymer fiber can be blended into the milled powder. When a polymer powder is used, the polymer powder and milled calcium phosphate powders can be ball milled together to produce a homogeneous mixed powder. Next, in step 206, the powder is pressed uniaxially in a mold until a solid form is created that can hold its shape. The solid form is then subjected to uniform pressing, such as cold isostatic pressing (CIP), warm isostatic pressing (WIP), or hot isostatic pressing (HIP) techniques known in the art. In some embodiments, step 207, warm isostatic pressing is used for powders including a polymer. In other embodiments, step 208, cold isostatic pressing is used. Isostatic pressing is performed at pressures between about 25,000 psi and about 50,000 psi. In some embodiments, isostatic pressing is performed at pressures between about 30,000 psi and about 44,000 psi. Use of isostatic pressing instead of uniaxial pressing applies a uniform force throughout the powder compact. This results in uniform packing and densification.

After pressing, in step 209 the implant optionally is sintered to further increase its strength. Sintering involves heating at high temperatures to fuse particles and/or modify grain size and/or promote crystallinity. For example, implants sintered at a temperature of about 1100° C. can have a compressive strength greater than 300 MPa, and implants sintered at a temperature of about 1400° C. can have a compressive strength of up to about 500 MPa. Although very strong, sintered implants are very hard and can be more crystalline and therefore less readily resorbable in vivo than non-sintered implants. Finally, in step 210, the pressed implant is machined to obtain the desired shape and size for implantation. After the machining stage, a bone regenerative protein optionally is added to the implant. For example, in some embodiments, the implant is immersed in a solution of a bone regenerative protein at room temperature for about one hour to achieve saturating free diffusion of the protein into the pores of the implant. Impregnation of the implant takes place at low temperatures, e.g., between about 0° C. and about 30° C., to avoid conversion of the calcium phosphate precursor into the product poorly-crystalline hydroxyapatite. This conversion occurs at about body temperature but does not proceed significantly at room temperature, meaning that the implant can be immersed in solution for about one hour at room temperature without substantial conversion of the calcium phosphate precursor to poorly-crystalline hydroxyapatite. The temperature ranges for body temperature and room temperature are well-understood in the art and can be, for example, between about 35° C. and about 40° C. for body temperature and between about 20° C. and about 25° C. for room temperature.

Figure 2:
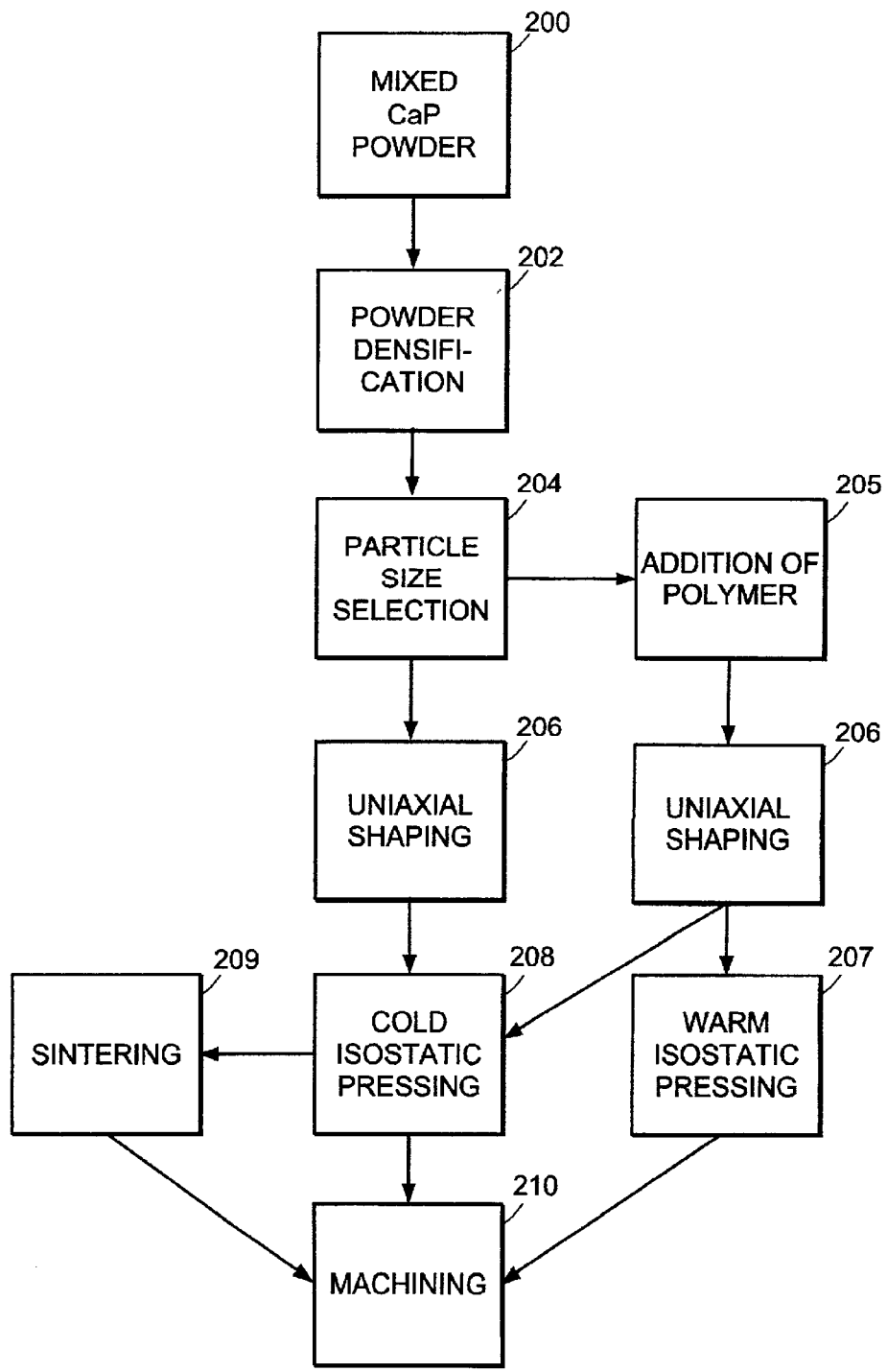
FIG. 2 is a flow diagram of a process for making implants of the invention.

The isostatic pressing of an intimately mixed homogenous powder, in a procedure as outlined in FIG. 2, affords good control over the porosity of the bone substitute material implants of the invention, allowing for mechanical consistency within each implant and across implants. The controlled, uniform mechanical properties of the bone substitute material implants of the invention provide an improvement over natural bone, which often possesses inconsistencies and non-isotropic properties. Pore size of the bone substitute material implants can be controlled by particle size selection of the calcium phosphate materials of the precursor powder and/or by selection of the isostatic pressing conditions used to press the implant, with smaller particle size and increased isostatic pressure corresponding to decreased pore size, as well as decreased overall porosity.

Controlled pore size is desirable, for example, to promote efficient uptake in vivo of biological molecules such as bone regenerative proteins, including, for example, bone morphogenetic proteins. For example, the pore size distribution of a calcium phosphate implant can be between about 30 Å and about 1 µm. Implants containing a polymer have micro and macro pore size distributions, due to the inclusion of two types of material, polymer and calcium phosphate. The macro pore distribution due to polymer powder particles can be, for example, between about 100 nm and about 10 µm, with smaller pore size distribution resulting from the calcium phosphate powder. The macro pore distribution can range up to about 100 µm for implants including a polymer fiber.

The overall porosity of the bone substitute material implants can be, for example, between about 5 percent and about 30 percent. Controlled low porosity corresponds to uniform high density and strength, such that bone substitute material implants of the invention are useful, for example, in spinal fusion applications that require great compressive strength and controlled mechanical properties. Because the porosity of the bone substitute material implants is controlled and uniform, defects in the implants are small, which further enhances the mechanical reliability, density, and strength of the implants. The compressive strength of calcium phosphate implants can be between about 60 MPa and about 100 MPa. Implants including a reinforcing polymer can have a compressive strength up to about 200 MPa, and sintered implants can have a compressive strength up to about 500 MPa. The implants also provide good shear strength, for example between about 6,000 N and about 10,000 N, and up to about 16,000 N for implants including a polymer. The implants maintain their strength upon exposure to fluid at body temperature, as demonstrated in Example 4 below. Retention of strength in the presence of fluid, which causes reaction between the precursor materials to form poorly-crystalline hydroxyapatite, is important for the implants of the invention, which are designed to impart strength in vivo. Further, the strength provided in the body by an implant of the invention is similar to the strength of natural bone, such that the implant provides sufficient support for the surrounding bone, but is not so strong that it causes the stress shielding problems associated with metal implants.

Those of skill in the art will understand that the shape of a bone substitute material implant of the invention is chosen based upon the application for which the implant is to be used. For example, particular implant shapes are known in the art for use in stabilizing and facilitating arthrodesis in various regions of the spine. The dimensions of the implant similarly vary by application and are determined based on the size, shape, type, and location of the bone being repaired, and the size and shape of the space into which an implant is to be inserted. For example, some implants for use in fusing adjacent spinal vertebrae are designed to fit into a space between the vertebrae, or to extend slightly beyond the space in order to engage the vertebrae on either side.

Figure 3:
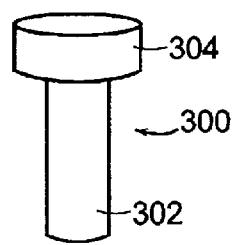
FIG. 3 is a side perspective view of a plug-shaped implant of the invention.
Figure 4A:
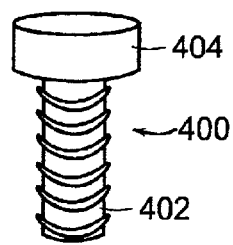
FIGS. 4A–B are side perspective views of screw-shaped implants of the invention.
Figure 4B:
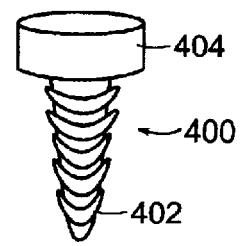
Figure 5:
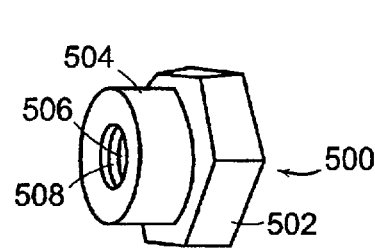
FIG. 5 is a perspective view of another implant of the invention.
Figure 6:
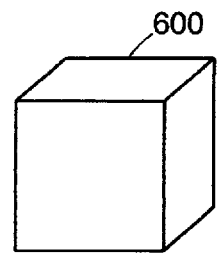
FIG. 6 is a perspective view of a cubical implant of the invention.

Non-limiting examples of useful shapes for implants of the invention are shown in FIGS. 1 and 3–6. For example, bone substitute material dowels, as shown in FIG. 1A, in the form of a solid cylinder 100, are useful for implantation in the spinal column. An alternative form for implants of the invention is a plug, as shown in FIG. 3. The plug 300 has a cylindrical body 302 and a cylindrical head 304 having a diameter greater than the diameter of the body 302. Other bone substitute material implants of the invention take the form of a screw, as shown in FIGS. 4A–B. The screw 400 has threads 402 and a head 404 having a diameter greater than the diameter of the threads 402. The threads 402 can be of constant diameter, as shown in FIG. 4A, or can taper, as shown in FIG. 4B. Another form for bone substitute material implants of the invention is shown in FIG. 5. The implant 500 has a hexagonal head 502 and a cylindrical body 504 having a diameter less than the diameter of the head 502. The cylindrical body 504 has a cylindrical shaft 506 containing internal threads 508. Still other bone substitute material implants of the invention are in the form of a cube 600, as shown in FIG. 6.

The following examples further illustrate certain embodiments of the present invention.

EXAMPLE 1

Synthesis of Amorphous Calcium Phosphate

A solution of 150 g disodium hydrogen phosphate heptahydrate ($Na_2HPO_4 \cdot 7H_2O$) in 2167 mL distilled water was prepared and stirred. 83.3 g NaOH, 50 g $NaHCO_3$, and 3.3 g sodium pyrophosphate decahydrate ($Na_4P_2O_7 \cdot 10H_2O$) were added sequentially to the solution to form solution 1.

A solution of 31.2 g calcium nitrate tetrahydrate ($Ca(NO_3)_2 \cdot 4H_2O$) in 833 mL distilled water was prepared and stirred. 1.7 g magnesium chloride hexahydrate ($MgCl_2 \cdot 6H_2O$) was added to the solution to form solution 2.

Solution 2 was poured quickly into solution 1 at room temperature and stirred for 1 minute. Precipitation was immediate and substantially complete. The pH of the suspension was 13±0.5, which was maintained to avoid conversion of the precipitate to an apatite or other more crystalline calcium phosphate. The precipitate was promptly separated from its mother solution by basket centrifugal filtration and washed with about 15 L distilled water. Completion of washing was confirmed by the last wash ionic conductivity <300 µs. A gel cake of about 100 g amorphous calcium phosphate was obtained. The wet cake was immediately lyophilized to preserve the amorphous structure during drying, which removed about 80% of the water. The lyophilized powder was calcinated at 450° C. for 1 hour. The Ca/P ratio of the product was less than 1.5.

EXAMPLE 2

Preparation of Dicalcium Phosphate Dihydrate 20 g diammonium hydrogen phosphate ($(NH_4)_2 \cdot HPO_4$) was dissolved in 1 L distilled water to prepare solution 3 with a concentration of 0.300 mol/L. It was verified that the pH of solution 3 was between 7.0 and 9.0.

35.5 g calcium nitrate tetrahydrate ($Ca(NO_3)_2 \cdot 4H_2O$) was dissolved in 0.5 L distilled water to prepare solution 4 with a concentration of 0.300 mol/L. It was verified that the pH of solution 4 was between 5.0 and 8.0.

Solution 4 was poured into solution 3, followed by stirring for about 2 minutes. It was verified that the pH of the resulting suspension was between 5.2 and 6.2. The suspension was filtered by vacuum filtration to form a uniform cake. The cake was washed three times with 750 mL distilled water (2.25 L total). When washing was complete, the cake was separated from the filter paper and dried in a laminar flow hood for 24 hours. The dried powder was milled through a 120 µm nominal pore size screen.

EXAMPLE 3

Bone Substitute Material Dowels 100 g (~250 mL) lots of a mixture of equal parts by weight amorphous calcium phosphate (ACP) and dicalcium phosphate dihydrate (DCPD) were ground into a homogeneous powder by ball milling in a 3440 mL alumina ceramic jar. Milling was performed using 750 mL of media (10 mm diameter balls of high purity zirconium oxide stabilized by $Y_2O_3$) at 100 rpm for 3 hours. The resultant powder was sieved to remove particles of size >125 µm. Solid cylindrical dowels 17 mm in diameter and 23 mm long were formed from the sieved powder using a uniaxial press. Uniaxial shaping was performed, creating a cylindrical shape by applying 0.25 tons of force to the powder in a die. Then isostatic pressing was performed between 30,000 psi and 44,000 psi, either cold (CIP) at room temperature, or warm (WIP) at about 66° C. Polymer powder or fiber, added after milling, was included in some dowels. Some dowels were sintered at 1100° C. in an argon atmosphere after isostatic pressing.

Table 1 presents compressive strength and shear strength data for the dowels. The data show that the dowels were significantly stronger than cancellous bone (2–5 MPa compressive strength), and about as strong cortical bone (100–160 MPa compressive strength), especially when polymer powder was included.

TABLE 1

| Dowel<br>50% ACP + 50% DCPD | Raw Load Data | | Calculated Stress Data | |
|---|---|---|---|---|
| | Compressive<br>Strength (N) | Shear<br>Strength (N) | Compressive<br>Strength (MPa) | Shear Strength<br>(MPa) |
| Cold Press | 21,253 | 9,625 | 67.25 | 26.15 |
| Sintered | 22,796 | 15,879 | 72.13 | 43.14 |
| + Polymer Powder* (warm press) | 35,477 | 15,468 | 112.26 | 42.03 |
| + Polymer Fibers** (cold press) | 22,436 | 7,294 | 71.00 | 19.82 |
| + Polymer Powder & Fibers (warm press) | 22,044 | 6,716 | 69.76 | 18.25 |

*20 wt. % Poly (D,L-Lactide-Co-Glycolide), 75–25%
**4 wt. % Polylactide chopped fibers

EXAMPLE 4

Bone Substitute Material Dowels with Copolymer Powder 100 g (~250 mL) lots of a mixture of equal parts by weight amorphous calcium phosphate and dicalcium phosphate dihydrate were ground into a homogeneous powder by ball milling in a 3440 mL alumina ceramic jar. Milling was performed using 750 mL of media (10 mm diameter balls of high purity zirconium oxide stabilized by $Y_2O_3$) at 100 rpm for three hours. The resultant powder was sieved to remove particles of size >125 µm. Between 0 and 30 weight percent of the powdered copolymer poly(lactide-co-glycolide), 75%–25%, was added to the sieved powder, and the mixture was milled for one hour at 100 rpm. Following the addition of the copolymer, dowels 17 mm in diameter and 23 mm long were formed from the powder using a uniaxial press. Uniaxial shaping was performed, creating a cylindrical shape by applying 0.25 tons of force to the powder in a die. Then isostatic pressing was performed for about one minute at either 30,000 psig or 44,000 psig. Cold isostatic pressing (CIP) at room temperature was used for dowels containing no copolymer, and warm isostatic pressing (WIP) at about 66° C. was used for dowels containing copolymer.

Table 2 presents data regarding some physical properties of the dowels. The data show that dowels pressed at greater pressure and dowels including more copolymer powder were less porous and had greater compressive strength. The data also show that the dowels maintained their strength upon exposure to fluid, as the free diffusion compressive strength after one hour of fluid exposure was similar to the initial compressive strength of the dry dowels.

TABLE 2

| % Co-polymer Powder | Iso Pressure (psig) | Compressive Strength (MPa) | | | Bulk Density (g/cc) | Porosity (%) | Fluid Absorbed after 1 hour at 22° C. (Vol. %) | Free Diffusion Compressive Strength after 1 hour at 22° C. (MPa) | | |
|---|---|---|---|---|---|---|---|---|---|---|
| | | n | Mean | Std. Dev. | | | | n | Mean | Std. Dev. |
| 0 | 30,000 | 6 | 83 | 8 | 1.97 | 24 | 14 | 5 | 98 | 6 |
| 0 | 44,000 | 5 | 120 | 19 | 2.03 | 21 | 20 | 5 | 124 | 21 |
| 3 | 30,000 | 2 | 109 | 10 | 2.04 | — | — | — | — | — |
| 3 | 44,000 | 8 | 160 | 18 | 2.07 | 16 | 12 | 4 | 149 | 20 |
| 5 | 44,000 | 6 | 133 | 18 | 2.09 | 17 | 10 | 4 | 127 | 34 |
| 7 | 44,000 | 9 | 128 | 32 | 2.11 | 17 | 6 | 4 | 129 | 35 |
| 10 | 44,000 | 4 | 181 | 15 | 2.15 | 11 | 6 | 4 | 145 | 22 |
| 20 | 30,000 | 3 | 123 | 8 | 1.95 | 11 | 9 | 5 | 105 | 4 |
| 20 | 44,000 | 3 | 150 | 7 | 2.02 | 7 | 3 | 3 | 136 | 5 |
| 30 | 30,000 | 3 | 119 | 12 | 1.87 | — | 2 | 4 | 116 | 6 |

As will be apparent to one of skill in the art from a reading of this disclosure, the present invention can be embodied in forms other than those specifically disclosed above without departing from the spirit or essential characteristics of the invention. The particular embodiments of the invention described above are, therefore, to be considered as illustrative and not restrictive. The scope of the invention is as set forth in the appended claims, rather than being limited to the examples contained in the foregoing description.

What is claimed is:

1. A bone implant comprising an unhydrated calcium phosphate precursor capable of forming poorly-crystalline hydroxyapatite in vivo upon hydration at the implantation site, wherein the precursor has a calcium to phosphorous atomic ratio between about 1.2 and about 1.68, and wherein the implant has a compressive strength of at least about 60 MPa.

2. The bone implant of claim 1, wherein the implant is a machined article.

3. The bone implant of claim 1, wherein the precursor comprises a first calcium phosphate in intimate mixture with a second calcium phosphate, the second calcium phosphate having a different calcium to phosphorous atomic ratio than the first calcium phosphate.

4. The bone implant of claim 1, wherein the precursor comprises a first calcium phosphate in intimate mixture with a second calcium phosphate, the second calcium phosphate having a different crystallinity that the first calcium phosphate.

5. The bone implant of claim 4, wherein the first calcium phosphate is an amorphous calcium phosphate, and wherein the second calcium phosphate has great crystallinity than the first calcium phosphate.

6. The bone implant of claim 5, wherein the first calcium phosphate has a calcium to phosphorous atomic ratio less than about 1.5.

7. The bone implant of claim 5, wherein the second calcium phosphate is selected from the group consisting of dicalcium phosphate dihydrate, calcium metaphosphate, heptacalcium phosphate, tricalcium phosphate, calcium pyrophosphate dihydrate, calcium pyrophosphate, and octacalcium phosphate.

8. The bone implant of claim 7, wherein the second calcium phosphate is dicalcium phosphate dihydrate.

9. The bone implant of claim 1, further comprising a biocompatible polymer powder.

10. The bone implant of claim 9, wherein the implant has a compressive strength of at least about 120 MPa.

11. The bone implant of claim 1, further comprising a biocompatible polymer fiber.

12. The bone implant of claim 11, wherein the implant has a compressive strength of at least about 120 MPa.

13. The bone implant of claim 1, wherein the implant has a compressive strength of at least about 120 MPa.

14. The bone implant of claim 1, further comprising a bone regenerative protein.

15. The bone implant of claim 1, wherein said precursor comprises nanometer-scale crystals of about 26 nm long and about 8 nm wide.

16. A bone implant comprising:
   (a) a first calcium phosphate that is an amorphous calcium phosphate; and
   (b) in intimate mixture with the first calcium phosphate, a second calcium phosphate having greater crystallinity than the first calcium phosphate;
   wherein the overall calcium to phosphorous atomic ratio is between about 1.2 and about 1.68 and said first and second calcium phosphates are unhydrated; and
   wherein the implant has a compressive strength of at least about 60 MPa.

17. The bone implant of claim 16, wherein the first calcium phosphate has a calcium to phosphorous atomic ratio less than about 1.5.

18. The bone implant of claim 16, wherein the second calcium phosphate is selected from the group consisting of dicalcium phosphate dihydrate, calcium metaphosphate, heptacalcium phosphate, tricalcium phosphate, calcium pyrophosphate dihydrate, calcium pyrophosphate, and octacalcium phosphate.

19. The bone implant of claim 18, wherein the second calcium phosphate is dicalcium phosphate dihydrate.

20. The bone implant of claim 16, further comprising a biocompatible polymer powder.

21. The bone implant of claim 20, wherein the implant has a compressive strength of at least about 120 MPa.

22. The bone implant of claim 16, further comprising a biocompatible polymer fiber.

23. The bone implant of claim 22, wherein the implant has a compressive strength of at least about 120 MPa.

24. The bone implant of claim 16, wherein the implant has a compressive strength of at least about 120 MPa.

25. The bone implant of claim 16, further comprising a bone regenerative protein.

26. The bone implant of claim 16, wherein said precursor comprises nanometer-scale crystals of about 26 nm long and about 8 nm wide.

27. A method of bone implantation comprising:
(a) providing a bone implant comprising an unhydrated calcium phosphate precursor capable of forming poorly-crystalline hydroxyapatite in vivo upon hydration at the implantation site, wherein the precursor has a calcium to phosphorous atomic ratio between about 1.2 and about 1.68, and wherein the implant has a compressive strength of at least about 60 MPa; and
(b) securing the bone implant at a site requiring implantation,
whereby the precursor undergoes conversion to poorly-crystalline hydroxyapatite at the implantation site.

28. The method of claim 27, wherein conversion of the precursor to poorly-crystalline hydroxyapatite is completed in a time between about 2 weeks and about 6 weeks after securing the bone implant at the implantation site.

29. The method of claim 27, wherein conversion of the precursor to poorly-crystalline hydroxyapatite occurs at about body temperature but does not proceed significantly at room temperature.

30. The method of claim 27, wherein the bone implant further comprises a bone regenerative protein that it delivered at the implantation site.

31. The method of claim 27, wherein said precursor comprises nanometer-scale crystals of about 26 nm long and about 8 nm wide.

32. A method of spinal fusion comprising:
(a) providing a bone implant comprising:
(i) a first calcium phosphate that is an amorphous calcium phosphate; and
(ii) in intimate mixture with the first calcium phosphate, a second calcium phosphate having greater crystallinity than the first calcium phosphate; wherein the overall calcium to phosphorous atomic ratio is between about 1.2 and about 1.68 and said first and second calcium phosphates are unhydrated; and
wherein the implant has a compressive strength of at least about 60 MPa; and
(b) securing the bone implant between adjacent spinal vertebrae to promote fusion of the vertebrae.

33. The method of claim 32, wherein said precursor comprises nanometer-scale crystals of about 26 nm long and about 8 nm wide.

34. A method of spinal fusion comprising:
(a) providing a bone implant comprising an unhydrated calcium phosphate precursor capable of forming poorly-crystalline hydroxyapatite in vivo upon hydration at the implant site, wherein the precursor has a calcium to phosphorous atomic ratio between about 1.2 and about 1.68, and wherein the implant has a compressive strength of at least about 60 MPa; and
(b) securing the bone implant between adjacent spinal vertebrae to promote fusion of the vertebrae.

35. The method of claim 34, wherein said precursor comprises nanometer-scale crystals of about 26 nm long and about 8 nm wide.

36. A method of bone implantation comprising:
(a) providing a bone implant comprising:
(i) a first calcium phosphate that is an amorphous calcium phosphate; and
(ii) in intimate mixture with the first calcium phosphate, a second calcium phosphate having a greater crystallinity than the first calcium phosphate; wherein the overall calcium to phosphorous atomic ratio is between about 1.2 and about 1.68 and said first and second calcium phosphates are unhydrated; and
wherein the implant has a compressive strength of at least about 60 MPa; and
(b) securing the bone implant at a site requiring implantation;
whereby the first and second calcium phosphates undergo conversion to poorly-crystalline hydroxyapatite upon hydration at the implantation site.

37. The method of claim 36, wherein conversion of the first and second calcium phosphates to poorly-crystalline hydroxyapatite is completed in a time between about 2 weeks and about 6 weeks after securing the bone implant at the implantation site.

38. The method of claim 36, wherein conversion of the precuror to poorly-crystalline hydroxyapatite occurs at about body temperature but does not proceed significantly at room temperature.

39. The method of claim 36, wherein the bone implant further comprises a bone regenerative protein that is delivered at the implantation site.

40. The method of claim 36, wherein said precursor comprises nanometer-scale crystals of about 26 nm long and about 8 nm wide.

* * * * *